United States Patent [19]

Kao et al.

[11] Patent Number: 5,118,678
[45] Date of Patent: Jun. 2, 1992

[54] CARBAMATES OF RAPAMYCIN

[75] Inventors: Wenling Kao, Paoli, Pa.; Robert L. Vogel, Stratford, N.J.; John H. Musser, Alameda, Calif.

[73] Assignee: American Home Products Corporation, New York, N.Y.

[21] Appl. No.: 686,728

[22] Filed: Apr. 17, 1991

[51] Int. Cl.$^5$ .................. A61K 31/395; C07D 491/06
[52] U.S. Cl. .................... 514/183; 514/321; 514/63; 540/452; 540/456
[58] Field of Search ................ 540/456, 452; 514/183, 514/321, 63

[56] References Cited

U.S. PATENT DOCUMENTS

| | | | |
|---|---|---|---|
| 3,929,992 | 12/1975 | Seghal et al. | 424/122 |
| 3,993,749 | 11/1976 | Seghal et al. | 424/122 |
| 4,316,885 | 2/1982 | Rakhit | 424/122 |
| 4,401,653 | 8/1983 | Eng | 424/114 |
| 4,650,803 | 3/1987 | Stella et al. | 546/90 |
| 4,885,171 | 12/1989 | Surendra et al. | 424/122 |

OTHER PUBLICATIONS

J. Antibiot. 28, 721-726 (1975).
J. Antibiot. 28, 727-732 (1975).
J. Antibiot. 31, 539-545 (1978).
Can. J. Physiol. Pharmacol. 55, 48 (1977).
FASEB 3,3411 (1989).
FASEB 3,5256 (1989).
Lancet 1183 (1978).
Med. Sci. Res. 17: 877 (1989).

Primary Examiner—Robert T. Bond
Attorney, Agent, or Firm—Arnold S. Milowsky

[57] ABSTRACT

A compound of the structure

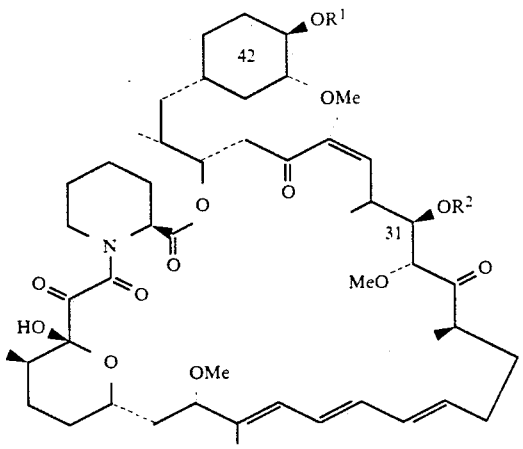

wherein
  $R^1$ and $R^2$ are each, independently, hydrogen or $-CONH(CR^3R^4)_n-X$;
  $R^3$ and $R^4$ are each, independently, hydrogen, alkyl, aralkyl, cycloalkyl, halogen, or trifluoromethyl;
  X ix hydrogen, lower alkyl, cycloalkyl, trifluoromethyl, nitro, alkoxy, carboalkoxy, aralkyl, halo, dialkylamino, thioalkyl, or Y;
  Y is a phenyl group which may be optionally mono-, di-, or tri- substituted with a group selected from alkyl, aralkyl, alkoxy, cyano, halo, nitro, carbalkoxy, trifluoromethyl, dialkylamino, or alkylthio;
  n=0-5;
  with the proviso that $R^1$ and $R^2$ are not both hydrogen and when n=0, X is lower alkyl, cycloalkyl, aralkyl, or Y;

or a pharmaceutically acceptable salt thereof when X is dialkylamino, which by virtue of its immunosuppressive activity is useful in treating transplantation rejection, host vs. graft disease, autoimmune diseases and diseases of inflammation; by virtue of its antitumor activity is useful in treating solid tumors; and by virtue of its antifungal activity is useful in treating fungal infections.

23 Claims, No Drawings

CARBAMATES OF RAPAMYCIN

BACKGROUND OF THE INVENTION

This invention relates to carbamates of rapamycin and a method for using them in the treatment of transplantation rejection, host vs. graft disease, autoimmune diseases, diseases of inflammation, solid tumors, and fungal infections.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Calne et al., Lancet 1183 (1978)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31-and 42- positions.

DESCRIPTION OF THE INVENTION

This invention provides derivatives of rapamycin which are useful as immunosuppressive, anti-inflammatory, antifungal, and antitumor agents having the structure

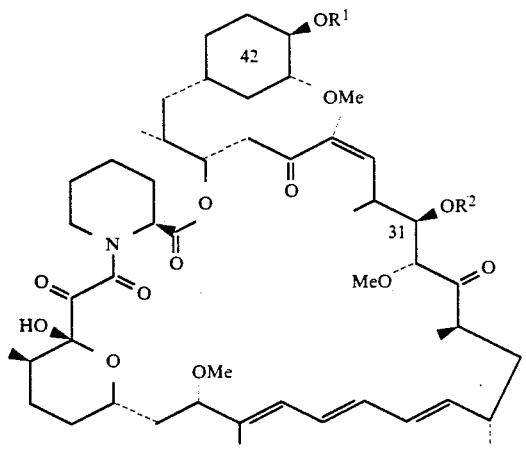

wherein
$R^1$ and $R^2$ are each, independently, hydrogen or $-CONH(CR^3R^4)_n-X$;

$R^3$ and $R^4$ are each, independently, hydrogen, alkyl of 1-6 carbon atoms, aralkyl of 7-10 carbon atoms, cycloalkyl of 3-8 carbon atoms, halogen, or trifluoromethyl;

X is hydrogen, lower alkyl of 1-6 carbon atoms, cycloalkyl of 3-8 carbon atoms, trifluoromethyl, nitro, alkoxy of 1-6 carbon atoms, carboalkoxy of 2-7 carbon atoms, aralkyl of 7-10 carbon atoms, halo, dialkylamino of 1-6 carbon atoms per alkyl group, thioalkyl of 1-6 carbon atoms, or Y;

Y is a phenyl group which may be optionally mono-, di-, or tri-substituted with a group selected from alkyl of 1-6 carbon atoms, aralkyl of 7-10 carbon atoms, alkoxy of 1-6 carbon atoms, cyano, halo, nitro, carbalkoxy of 2-7 carbon atoms, trifluoromethyl, dialkylamino of 1-6 carbon atoms per alkyl group, or alkylthio of 1-6 carbon atoms;

n = 0-5;

with the proviso that $R^1$ and $R^2$ are not both hydrogen and when n=0, X is lower alkyl of 1-6 carbon atoms, cycloalkyl of 3-8 carbon atoms, aralkyl of 7-10 carbon atoms, or Y;

or a pharmaceutically acceptable salt thereof when X is dialkylamino of 1-6 carbon atoms per alkyl group.

The pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

Of these compounds, preferred members are those in which $R^2$ is hydrogen; those in which $R^1$ is hydrogen; those in which n is 0 and X is Y; those in which $R^2$ is hydrogen, n is 0, and X is Y; and those in which n is 0, X is Y, and Y is phenyl, 4-fluorophenyl, 2,4-difluorophenyl, 4-nitrophenyl, or 4-methylphenyl.

The compounds of this invention carbamylated at the 42-position or at both the 31- and 42-positions can be prepared by reacting rapamycin with an isocyanate having the general structure $$O=C=N-(CR^3R^4)_n-X$$

in the presence of a base, such as pyridine.

The 31-carbamylated compounds of this invention can be prepared by protecting the 42-alcohol of rapamycin with a protecting group, such as with a tert-butyl dimethylsilyl group, followed by carbamylation of the 31-position with an isocyanate with the general structure shown above. Removal of the protecting group provides the 31-carbamylated compounds. In the case of the tert-butyl dimethylsilyl protecting group, deprotection can be accomplished under mildly acidic conditions.

Having the 31-position carbamylated and the 42-position deprotected, the 42-position can be reacted with a different isocyanate than was reacted with the 31-alcohol, to give compounds having different carbamates at the 31- and 42-positions. Alternatively, the 42-carbamylated compounds, prepared as described above, can be reacted with a different isocyanate to provide compounds having different carbamates at the 31- and 42-positions.

The isocyanates used to prepare the compounds of the invention are commercially available or can be prepared by methods that are disclosed in the literature.

Immunosuppressive activity was evaluated in an in vitro standard pharmacological test procedure to measure lymphocyte proliferation (LAF) and in two in vivo standard pharmacological test procedures. The first in vivo procedure was a popliteal lymph node (PLN) test procedure which measured the effect of compounds of this invention on a mixed lymphocyte reaction and the second in vivo procedure evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from non-drug treated controls. The results are expressed as an $IC_{50}$.

$$\frac{^3H\text{-control thymus cells} - H^3\text{-rapamycin-treated thymus cells}}{^3H\text{-control thymus cells} - H^3\text{-test compound-treated cells}}$$

A mixed lymphocyte reaction (MLR) occurs when lymphoid cells from genetically distinct animals are combined in tissue culture. Each stimulates the other to undergo blast transformation which results in increased DNA synthesis that can be quantified by the incorporation of tritiated thymidine. Since stimulating a MLR is a function of disparity at Major Histocompatibility antigens, an in vivo popliteal lymph node (PLN) test procedure closely correlates to host vs. graft disease. Briefly, irradiated spleen cells from BALB/c donors are injected into the right hind foot pad of recipient C3H mice. The drug is given daily, p.o. from Day 0 to Day 4. On Day 3 and Day 4, tritiated thymidine is given i.p., b.i.d. On Day 5, the hind popliteal lymph nodes are removed and dissolved, and radioactivity counted. The corresponding left PLN serves as the control for the PLN from the injected hind foot. Percent suppression is calculated using the non-drug treated animals as allogenic control. Rapamycin at a dose of 6 mg/kg, p.o. gave 86% suppression, whereas cyclosporin A at the same dose gave 43% suppression. Results are expressed by the following ratio:

$$\frac{^3H\text{-PLN cells control C3H mouse} - ^3H\text{-PLN cells rapamycin-treated C3H mouse}}{^3H\text{-PLN cells control C3H mouse} - ^3H\text{-PLN cells test compound-treated C3H mouse}}$$

The second in vivo test procedure is designed to determine the survival time of pinch skin graft from male DBA/2 donors transplanted to male BALB/c recipients. The method is adapted from Billingham R. E. and Medawar P. B., J. Exp. Biol. 28:385-402, (1951). Briefly, a pinch skin graft from the donor is grafted on the dorsum of the recipient as a homograft, and an autograft is used as control in the same region. The recipients are treated with either varying concentrations of cyclosporin A as test control or the test compound, intraperitoneally. Untreated recipients serve as rejection control. The graft is monitored daily and observations are recorded until the graft becomes dry and forms a blackened scab. This is considered as the rejection day. The mean graft survival time (number of days ±S.D.) of the drug treatment group is compared with the control group.

The following table summarizes the results of representative compounds of this invention in these three standard test procedures.

TABLE 1

| Compound | LAF $IC_{50}$ (nM) | PLN (ratio) | Skin Graft (days + SD) |
|---|---|---|---|
| Example 1 | 8.6 | 0.71 | 8.5 ± 1.6 |
| Example 2 | 3.9 | 0.47 | 8.5 ± 1.2 |
| Example 3 | >1000 | + | + |
| Example 4 | 57.9 | 0.90 | + |
| Example 5 | 3%** | + | + |
| Example 6 | 10.4 | 0.25 | 8.3 ± 1.0 |
| Example 7 | + | + | + |
| Example 8 | 7.4 | + | 8.8 ± 1.3 |
| Example 9 | 8.7 | 0.72 | 8.0 ± 1.7 |
| Example 10 | >1000 | + | + |
| Example 11 | >1000 | + | − |
| Example 12 | >1000 | + | − |
| Example 14 | >1000 | + | + |
| Example 15 | >1000 | − | + |
| Rapamycin | 3.2-9.4 | 1.00 | 12.0 ± 1.7 |

− Not evaluated.
** Percent inhibition at 100 nM.

The results of these standard pharmacological test procedures demonstrate immunosuppressive activity both in vitro and in vivo for the compounds of this invention. Positive ratios in the LAF and PLN test procedures indicate suppression of T cell proliferation. As a transplanted pinch skin grafts are typically rejected within 6-7 days without the use of an immunosuppressive agent, the increased survival time of the skin graft when treated with the compounds of this invention further demonstrates their utility as immunosuppressive agents.

Because the compounds of this invention are structurally similar to rapamycin and have a similar activity profile to rapamycin, the compounds of this invention also are considered to have antitumor and antifungal activities.

Based on the results of these standard pharmacological test procedures, the compounds are useful in the treatment of transplantation rejection such as, heart, kidney, liver, bone marrow, and skin transplants; autoimmune diseases such as, lupus, rheumatoid arthritis, diabetes mellitus, myasthenia gravis, and multiple sclerosis; and diseases of inflammation such as, psoriasis, dermatitis, eczema, seborrhea, inflammatory bowel disease, and eye uveitis; solid tumors; and fungal infections.

The compounds may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

In addition, the compounds of this invention may be employed as a solution, cream, or lotion by formulation with pharmaceutically acceptable vehicles containing 0.1-5 percent, preferably 2%, of active compound which may be administered to a fungally affected area.

The following examples illustrate the preparation of representative compounds of this invention.

EXAMPLE 1

Rapamycin 42-ester with (4-fluorophenyl)carbamic acid

A solution of 70 mg of rapamycin in 1 mL of pyridine was treated at 0° under anhydrous conditions with 50 mg of parafluorophenyl isocyanate in 1.5 ml of pyridine. After stirring at 0° for 5 hours, the reaction mixture was diluted with 20 ml of 2N HCl at 0° and extracted with ethyl acetate. The ethyl acetate extract was washed with brine, dried with magnesium sulfate and evaporated. The residue was chromatographed on silica gel. Elution with 30% ethyl acetate in benzene afforded 15 mg of the title compound as a white solid, mp 99°-103°.

IR=KBr max 3440 (OH), 1740 (C=O), 1625 (amide C=O), 1460, 1855, 1200, 1070, 990 cm$^{-1}$. $^1$H NMR (CDCl$_3$, 400 MHz), δ7.38 (t, 2H, aromatic protons, ortho to fluorine), 7.00 (t, 2H, aromatic protons meta to fluorine), 3.39 (s, 3H, CH$_3$O), 3.33 (s, 3H, CH$_3$O); 3.14 (s, 3H CH$_3$O). MS (neg. ion FAB) 1050 (M$^-$), 590, 458, 167.

EXAMPLE 2

Rapamycin 42-ester with phenylcarbamic acid

A solution of 100 mg of rapamycin in 0.8 ml of pyridine was treated at 0° under anhydrous conditions with 60 mg of phenyl isocyanate in 0.5 ml of pyridine. After stirring at 0° anhydrous for 5 hours, the reaction mixture was diluted with 20 ml of 2N HCl at 0° and extracted with ethyl acetate. The ethyl acetate extract was washed with brine, dried with magnesium sulfate and evaporated. The residue was chromatographed on silica gel. Elution with 25% ethyl acetate in benzene afforded 65 mg of the title compound as a white solid, mp 106°-109°.

IR=KBr max 3400 (OH), 1725 (C=O), 1645 (amide C=O), 1600 (aromatic) 1540, 1440, 1315, 1080, 990 and 750 (aromatic). $^1$H NMR (CDCl$_3$, 400 MHz), δ7.40 (t, 2H, aromatic, ortho to NH), 7.32 (t, 2H, aromatic, 3.34 (s, 3H, CH$_3$O), 3.14 (s, 3H, CH$_3$O). MS (neg. ion FAB) 1032 (M$^-$), 590, 321, 167.

EXAMPLE 3

Rapamycin-31,42-diester with [4-(trifluoromethyl)phenyl]carbamic acid

A solution of 0.45 g 4-(trifluoromethyl)phenylisocyanate in 5 mL dry pyridine was added to a solution of 1.00 g rapamycin in 10 mL dry pyridine at 0° C., and the resulting solution was stirred at 0°-5° C. for 3.5 hours. Cold 2N HCl (75 mL) was added and the product was extracted into ethyl acetate, which was washed with brine, dried over magnesium sulfate and evaporated to dryness. The residue was chromatographed on silica gel. Elution with 10% ethyl acetate in methylene chloride afforded 0.63 g of 31,42-diester as a white solid, m.p. 147°-195° C. IR(KBr): 3400 (OH), 1730 (C=O), 1615, 1530, 1320, 1210, 1110, 1060 and 840 cm$^{-1}$. $^1$H NMR (CDCl$_3$, 400 MHz): 7.46-7.57 (complex, 8H, aromatic), 3.38 (s, 3H, OCH$_3$), 3.36 (s, 3H, OCH$_3$), 3.16 (s, 3H, OCH$_3$), MS (neg ion FAB): 1287 (M$^-$), 1081, 894, 590, 321.

The following representative compounds can be prepared from rapamycin and the appropriate isocyanate by employing the method used to prepare the title compound in Example 3.

Rapamycin-31,42-diester with (phenylmethyl)carbamic acid
Rapamycin-31,42-diester with cyclohexylcarbamic acid
Rapamycin-31,42-diester with methylcarbamic acid
Rapamycin-31,42-diester with 2-propylcarbamic acid
Rapamycin-31,42-diester with trifluoromethylcarbamic acid
Rapamycin-31,42-diester with 2-nitroethylcarbamic acid
Rapamycin-31,42-diester with [4-(N,N-dimethyl)butyl]carbamic acid
Rapamycin-31,42-diester with [2-(carbomethoxy)ethyl]carbamic acid Rapamycin-31,42-diester with [4-(methylthio)butyl]carbamic acid Rapamycin-31,42-diester with [3-ethyl-4-(4-nitrophenyl)butylcarbamic acid

EXAMPLE 4

Rapamycin-42-ester with [4-(trifluoromethyl)phenyl]carbamic acid

Continued elution of the residue described in Example 3 with 30% ethyl acetate in methylene chloride afforded 0.20 g 42-monoester as a white solid, mp 144°–172° IR (KBr): 3450 (OH), 1730 (C=O), 1650, 1615, 1535, 1445, 1315, 1210, 1110, 1050, 980 and 835 cm$^{-1}$. $^1$H NMR (CDCl$_3$, 400 MHz): δ7.55 (d, 2H, aromatic), 7.50 (d, 2H, aromatic), 3.39 (s, 3H, OCH$_3$), 3.34 (s, 3H, OCH$_3$), 3.14 (s, 3H, OCH$_3$). MS (neg ion FAB): 1100 (M−), 590, 321, 160.

The following representative compounds can be prepared from rapamycin and the appropriate isocyanate by employing the method used to prepare the title compound in Example 4.

Rapamycin-42-ester with (phenylmethyl)carbamic acid
Rapamycin-42-ester with cyclohexylcarbamic acid
Rapamycin-42-ester with methylcarbamic acid
Rapamycin-42-ester with 2-propylcarbamic acid
Rapamycin-42-ester with trifluoromethylcarbamic acid
Rapamycin-42-ester with 2-nitroethylcarbamic acid
Rapamycin-42-ester with [4-(N,N-dimethyl)butyl]carbamic acid
Rapamycin-42-ester with [2-(carbomethoxy)ethyl]carbamic acid
Rapamycin-42-ester with [4-(methylthio)butyl]carbamic acid
Rapamycin-42-ester with [3-ethyl-4-(4-nitrophenyl)-butylcarbamic acid

EXAMPLE 5

Rapamycin-31,42-diester with (4-nitrophenyl)carbamic acid

A solution of 0.38 g 4-nitrophenylisocyanate in 4 mL pyridine was added to a solution of 1.16 g rapamycin in 11 mL pyridine at 0° and stirred at 0° for 15 minutes, then warmed to 20° over 15 minutes and stirred at 20° for 1.5 hours. Cold 2N HCl (75 mL) was added, the products were extracted into ethyl acetate, washed with brine, dried over MgSO$_4$ and evaporated to dryness. The residue was chromatographed on silica gel; elution with 10% ethyl acetate in methylene chloride afforded 160 mg of the diester as a yellow solid, mp 164°–171°. IR (KBr): 3380 (OH), 2910, 1725 (C=O), 1635, 1590, 1500, 1320, 1200 and 850 cm$^{-1}$. $^1$H NMR (CDCl$_3$, 400 MHz): δ8.20 (d, 4H, aromatic), 7.57 (d, 2H, aromatic), 7.53 (d, 2H, aromatic), 3.38 (s, 3H, OCH$_3$), 3.37 (s, 3H, OCH$_3$), 3.16 (s, 3H, OCH$_3$). MS (neg ion FAB): 1241 (M−), 1058, 590.

EXAMPLE 6

Rapamycin-42-ester with (4-nitrophenyl)carbamic acid

Further elution of the residue described in Example 5 with 30% ethyl acetate in methylene chloride afforded 380 mg of the 42-monoester as a yellow solid, mp 137°–144°. IR (KBr): 3420 (OH), 2910, 1725 (C=O), 1500, 1320, 1205 and 840 cm$^{-1}$. NMR (CDCl$_3$, 400 MHz): δ8.20 (d, 2H, aromatic), 7.56 (d, 2H, aromatic), 3.39 (s, 3H, OCH$_3$), 3.34 (s, 3H, OCH$_3$), 3.14 (s, 3H, OCH$_3$). MS (neg ion FAB): 1077 (M−), 590, 321.

EXAMPLE 7

Rapamycin-31,42-diester with (4-methylphenyl)carbamic acid

A solution of 1.04 g 4-methylphenylisocyanate in 3 mL pyridine was added to a solution of 2.20 g rapamycin in 8 mL pyridine at 0° and stirred at 0° for 3.5 hours. Cold 2N HCl (180 mL) was added, the products were extracted into ethyl acetate, washed with brine, dried over MgSO$_4$ and evaporated to dryness. The reside was chromatographed on silica gel; elution with 10% ethyl acetate in methylene chloride afforded 300 mg of 31,42-diester as a yellow solid, mp 129°–145°.

IR(KBr): 3400 (OH), 2920, 1725 (C=O), 1645, 1520, 1450, 1215, 1200 and 812 cm$^{-1}$. NMR (CDCl$_3$, 400 MHz): δ7.27 (complex, 4H, aromatic), 7.10 (complex, 4H, aromatic), 3.38 (s, 3H, OCH$_3$), 3.35 (s, 3H, OCH$_3$), 3.16 (s, 3H, OCH$_3$), 2.30 (s, 3H, ArCH$_3$), 2.28 (s, 3H, ArCH$_3$). MS (neg ion FAB): 1179 (M−), 1027.

EXAMPLE 8

Rapamycin-42-ester with (4-methylphenyl)carbamic acid

Further elution of the residue described in Example 7 with 30% ethyl acetate in methylene chloride afforded 200 mg of the 42-monoester as a yellow solid, mp 123°–135°. IR (KBr): 3420 (OH), 2930, 1720 (C=O), 1640, 1520, 1440, 1220, 1203, and 1055 cm$^{-1}$. NMR (CDCl$_3$, 400 MHz): δ7.27 (d, 2H, aromatic), 7.10 (d, 2H, aromatic), 3.40 (s, 3H, OCH$_3$), 3.34 (s, 3H, OCH$_3$), 3.14 (s, 3H, OCH$_3$), 2.30 (s, 3H, ArCH$_3$). MS (neg ion FAB): 1046 (M−), 590, 321.

EXAMPLE 9

Rapamycin-42-ester with (2,4-difluorophenyl)carbamic acid

A solution of 0.24 g rapamycin and 0.10 g 2,4-difluorophenylisocyanate in 6 mL pyridine was stirred for 45 minutes at 0°. Cold 2N HCl (50 mL) was added, the product was extracted into ethyl acetate, washed with brine, dried over MgSO$_4$ and evaporated to dryness. Chromatography on silica gel using 25% ethyl acetate in methylene chloride afforded 69 mg of 42-ester as a white solid, mp 109°–114°. IR (KBr): 3420 (OH), 2910, 1720 (C=O), 1635, 1520, 1215, 1085 and 975 cm$^{-1}$. NMR (CDCl$_3$, 400 MHz): δ6.84 (complex, 2H, aromatic), 6.69 (complex, 1H, aromatic), 3.39 (s, 3H, OCH$_3$), 3.33 (s, 3H, OCH$_3$), 3.14 (s, 3H, OCH$_3$). MS (neg ion FAB): 1068 (M−), 590, 321.

EXAMPLE 10

Rapamycin-31,42-diester with (2,4-difluorophenyl)carbamic acid

A solution of 0.20 g rapamycin and 0.14 g 2,4-difluorophenylisocyanate in 10 mL pyridine was stirred 5 hours at 20°. Cold 2N HCl (50 mL) was added, the product was extracted into ethyl acetate, washed with brine and dried over MgSO$_4$. The solvent was evaporated off and the residue chromatographed on silica gel using 10% ethyl acetate in methylene chloride yielded 0.20 g of title compound as a pale yellow solid, mp 115°–123°. IR (KBr): 3420 (OH), 2910, 1725 (C=O), 1638, 1523, 1212, 1090 and 835 cm$^{-1}$. NMR (CDCl$_3$, 400 MHz): δ6.85 (complex, 4H, aromatic), 6.70 (complex, 2H, aromatic), 3.39 (s, 3H, OCH$_3$), 3.36 (s, 3H, OCH₃), 3.15 (s, 3H, OCH₃). MS: (neg ion FAB): 1223 (M⁻), 1049, 590, 321.

EXAMPLE 11

Rapamycin-31,42-diester with phenylcarbamic acid

A solution of 0.50 g rapamycin and 0.19 g phenylisocyanate in 10 mL pyridine was stirred at 20° for 16 hours. Cold 2N HCl (100 mL) was added and the product was extracted into ethyl acetate, washed with brine and dried over MgSO₄. The solvent was removed and the residue chromatographed on silica gel using 10% ethyl acetate in methylene chloride, yielded 0.32 g title compound as a white solid, mp 139°–148°. IR(KBr): 3330 (OH), 2920, 1720 (C=O), 1670, 1590, 1520, 1430, 1205, 745 and 685 cm⁻¹. NMR (CDCl₃, 400 MHz): δ7.27–7.40 (complex, 8H, aromatic), 7.06 (complex, 2H, aromatic), 3.39 (s, 3H, OCH₃), 3.37 (s, 3H, OCH₃), 3.16 (s, 3H, OCH₃). MS (neg ion FAB): 1151 (M⁻), 1013, 590, 321.

EXAMPLE 12

Rapamycin-31,42-diester with (4-fluorophenyl)carbamic acid

A solution of 1.54 g rapamycin and 0.68 g 4-fluorophenylisocyanate in 10 mL pyridine was stirred at 0° for 4.5 hours. Cold 2N HCl (100 mL) was added, the product was extracted into ethyl acetate, washed with brine, dried over MgSO₄, evaporated to dryness, and chromatographed on silica gel using 10% ethyl acetate in methylene to afford 0.65 g product as a white solid, mp 129°–140°. IR (KBr): 3430 (OH), 2920, 1725 (C=O), 1640, 1505, 1200 and 825 cm⁻¹. NMR (CDCl₃, 400 MHz): δ7.33 (complex, 4H, aromatic), 6.99 (t, 4H, aromatic), 3.38 (s, 3H, OCH₃), 3.35 (s, 3H, OCH₃), 3.16 (s, 3H, OCH₃). MS (neg ion FAB): 1187 (M⁻), 1031, 590, 321.

EXAMPLE 13

Rapamycin-42-tert-butyldimethylsilyl ether

Rapamycin (0.914 g) was added to a solution of 0.204 g imidazole and 0.165 g tert-butyldimethylsilyl chloride in 4 mL dimethylformamide at 0° and stirred under nitrogen for 16 hours at 20°. Brine (100 mL) was added, the product was extracted into ether, washed with brine, dried over MgSO₄ and evaporated. Chromatography on silica gel afforded 0.65 g of the title compound as a white solid. IR(KBr): 3430 (OH), 2920, 1715 (C=O), 1645, 1105, 985, 870, 842 and 775 cm⁻¹. NMR (CDCl₃, 400 MHz): δ3.41 (s, 3H, OCH₃), 3.34 (s, 3H, OCH₃), 3.14 (s, 3H, OCH₃), 0.886 (s, 9H, t-Bu), 0.074 (s, 3H, SiCH₃), 0.059 (s, 3H, SiCH₃). MS (neg ion FAB): 1027 (M⁻), 590, 435.

EXAMPLE 14

Rapamycin-42-tert-butyldimethylsilyl ether-31-ester with (2,4-difluorophenyl)carbamic acid A solution of 0.38 g of rapamycin-42-tert-butyl-dimethylsilyl ether and (2,4-difluorophenyl)isocyanate in 6 mL pyridine was stirred at 20 for 16 hours. Cold 2N HCl (75 mL) was added, the product was extracted into ethyl acetate, washed with brine, dried over MgSO₄, evaporated and the residue chromatographed on silica gel using 2% ethyl acetate in methylene chloride to afford 150 mg of title compound as a white solid, mp 112°–122°. IR(KBr): 3440 (OH), 2910, 1745 (C=O), 1640, 1520, 1090, 840 and 765 cm⁻¹. NMR (CDCl₃, 400 MHz): δ6.84 (complex, 3H, aromatic), 3.41 (s, 3H, OCH₃), 3.36 (s, 3H, OCH₃), 3.15 (s, 3H, OCH₃), 0.88 (pH, t-butyl), 0.075 (3H, SiCH₃), 0.061 (3H, SiCH₃). MS (neg ion FAB): 1182 (M⁻), 1027, 1008, 590, 435.

The following representative compounds can be prepared from rapamycin and the appropriate isocyanate by employing the method used to prepare the title compound in Example 14.

Rapamycin-42-tert-butyldimethylsilyl ether-31-ester with (phenylmethyl)carbamic acid Rapamycin-42-tert-butyldimethylsilyl ether-31-ester with hexylcarbamic acid Rapamycin-42-tert-butyldimethylsilyl ether-31-ester with difluoromethylcarbamic acid Rapamycin-42-tert-butyldimethylsilyl ether-31-ester with [4-(N,N-dimethyl)butyl]carbamic acid Rapamycin-42-tert-butyldimethylsilyl ether-31-ester with [4-(carbomethoxy)butyl]carbamic acid Rapamycin-42-tert-butyldimethylsilyl ether-31-ester with [2-(phenylmethyl)butyl]carbamic acid

EXAMPLE 15

Rapamycin-31-ester with (2,4-difluorophenyl)carbamic acid

Rapamycin-42-tert-butyldimethylsilyl ether-31-ester with (2,4-difluorphenyl)carbamic acid (0.60 g) was stirred for 16 hours at 20° in a solution of 4 mL tetrahydrofuran, 4 mL water and 12 mL acetic acid. After dilution with 100 mL water, the product was extracted into methylene chloride, washed with brine, dried over MgSO₄ and evaporated to an oil, which was chromatographed on silica gel using 30% ethyl acetate in methylene chloride to afford 220 mg of title compound as a white solid, mp 103°–117°. IR (KBr): 3440, 2920, 1735 (C=O), 1640, 1525, 1090 and 840 cm⁻¹. NMR (CDCl₃, 400 MHz): δ6.85 (complex, 3H, aromatic), 3.40 (s, 3H, OCH₃), 3.36 (s, 3H, OCH₃), 3.15 (s, 3H, OCH₃). MS (neg ion FAB): 1068 (M⁻), 894, 590, 128.

The following representative compounds can be prepared from rapamycin and the appropriate isocyanate by employing the method used to prepare the title compound in Example 15.

Rapamycin-31-ester with (phenylmethyl)carbamic acid

Rapamycin-31-ester with hexylcarbamic acid

Rapamycin-31-ester with difluoromethylcarbamic acid

Rapamycin-31-ester with [4-(N,N-dimethyl)butyl]carbamic acid

Rapamycin-31-ester with [4-(carbomethoxy)butyl]carbamic acid

Rapamycin-31-ester with [2-(phenylmethyl)butyl]carbamic acid

What is claimed is:

1. A compound of the formula

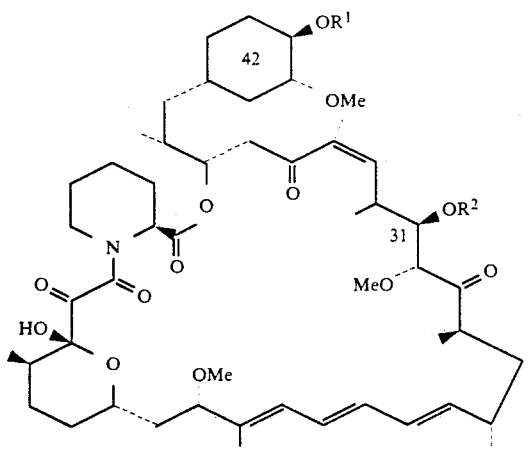

wherein
- R¹ and R² are each, independently, hydrogen or —CONH(CR³R⁴)$_n$—X;
- R³ and R⁴ are each, independently, hydrogen, alkyl of 1-6 carbon atoms, phenylalkyl of 7-10 carbon atoms, cycloalkyl of 3-8 carbon atoms, halogen, or trifluoromethyl;
- X is hydrogen, lower alkyl of 1-6 carbon atoms, cycloalkyl of 3-8 carbon atoms, trifluoromethyl nitro, alkoxy of 1-6 carbon atoms, carboalkoxy of 2-7 carbon atoms, phenylalkyl of 7-10 carbon atoms, halo, dialkylamino of 1-6 carbon atoms per alkyl group, thioalkyl of 1-6 carbon atoms, or Y;
- Y is a phenyl group which may be optionally mono-, di-, or tri-substituted with a group selected from alkyl of 1-6 carbon atoms, phenylalkyl of 7-10 carbon atoms, alkoxy of 1-6 carbon atoms, cyano, halo, nitro, carbalkoxy of 2-7 carbon atoms, trifluoromethyl, dialkylamino of 1-6 carbon atoms per alkyl group, or alkylthio of 1-6 carbon atoms;
- n=0-5;
- with the proviso that R¹ and R² are not both hydrogen and when n=0, X is lower alkyl of 1-6 carbon atoms, cycloalkyl of 3-8 carbon atoms, phenylalkyl of 7-10 carbon atoms, or Y;

or a pharmaceutically acceptable salt thereof when X is dialkylamino of 1-6 carbon atoms per alkyl group.

2. A compound of claim 1 where R¹ is hydrogen.
3. A compound of claim 1 where R² is hydrogen.
4. A compound of claim 1 where n is 0 and X is Y.
5. A compound of claim 1 where R² is hydrogen, n is 0, and X is Y.
6. A compound of claim 1 where n is 0, X is Y, and Y is phenyl, 4-fluorophenyl, 2,4-diflurophenyl, 4-nitrophenyl, or 4-methylphenyl.
7. A compound of claim 1 which is rapamycin 42-ester with (4-fluorophenyl)carbamic acid.
8. A compound of claim 1 which is rapamycin 42-ester with phenylcarbamic acid.
9. A compound of claim 1 which is rapamycin-31,42-diester with [4(trifluoromethyl)phenyl]carbamic acid.
10. A compound of claim 1 which is rapamycin-42-ester with [4-(trifluoromethyl)phenyl]carbamic acid.
11. A compound of claim 1 which is rapamycin-31,42-diester with (4-nitrophenyl)carbamic acid.
12. A compound of claim 1 which is rapamycin-42-ester with (4-nitrophenyl)carbamic acid.
13. A compound of claim 1 which is rapamycin-31,42-diester with (4-methylphenyl)carbamic acid.
14. A compound of claim 1 which is rapamycin-42-ester with (4-methylphenyl)carbamic acid.
15. A compound of claim 1 which is rapamycin-42-ester with (2,4-difluorophenyl)carbamic acid.
16. A compound of claim 1 which is rapamycin-31,42-diester with (2,4-difluorophenyl)carbamic acid.
17. A compound of claim 1 which is rapamycin-31,42-diester with phenylcarbamic acid.
18. A compound of claim 1 which is rapamycin-31,42-diester with (4-fluorophenyl)carbamic acid.
19. A compound of claim 1 which is rapamycin-31-ester with (2,4-difluorophenyl)carbamic acid.
20. A compound which is rapamycin-42-tert-butyldimethylsilyl ether-31-ester with (2,4-difluorophenyl)-carbamic acid.
21. A method of treating transplantation rejection, host vs. draft disease, autoimmune diseases, and diseases of inflammation in a mammal by administering an effective amount of a compound having the formula

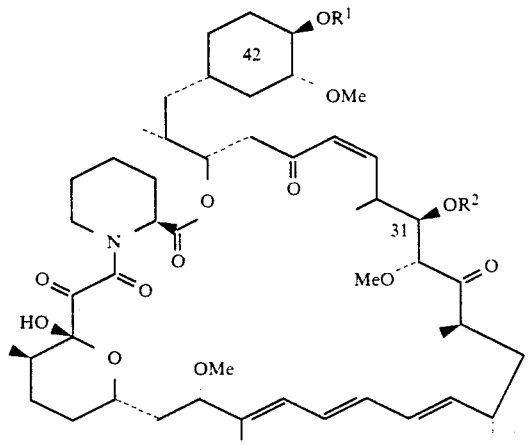

wherein
- R¹ and R² are each, independently, hydrogen or —CONH(CR³R⁴)$_n$—X;
- R³ and R⁴ are each, independently, hydrogen, alkyl of 1-6 carbon atoms, phenylalkyl of 7-10 carbon atoms, cycloalkyl of 3-8 carbon atoms, halogen, or trifluoromethyl;
- X is hydrogen, lower alkyl of 1-6 carbon atoms, cycloalkyl of 3-8 carbon atoms, trifluoromethyl nitro, alkoxy of 1-6 carbon atoms, carboalkoxy of 2-7 carbon atoms, phenylalkyl of 7-10 carbon atoms, halo, dialkylamino of 1-6 carbon atoms per alkyl group, thioalkyl of 1-6 carbon atoms, or Y;
- Y is a phenyl group which may be optionally mono-, di-, or tri-substituted with a group selected from alkyl of 1-6 carbon atoms, phenylalkyl of 7-10 carbon atoms, alkoxy of 1-6 carbon atoms, cyano, halo, nitro, carbalkoxy of 2-7 carbon atoms, trifluoromethyl, dialkylamino of 1-6 carbon atoms per alkyl group, or alkylthio of 1-6 carbon atoms;
- n=0-5;
- with the proviso that R¹ and R² are not both hydrogen and when n=0, X is lower alkyl of 1-6 carbon atoms, cycloalkyl of 3-8 carbon atoms, phenylalkyl of 7-10 carbon atoms, or Y;

or a pharmaceutically acceptable salt thereof when X is dialkylamino of 1-6 carbon atoms per alkyl group.

22. A pharmaceutical composition for use as an immunosuppressive agent comprising an immunosuppressive amount of a compound of claim 1.
23. A composition as claimed in claim 22 in unit dosage form.

* * * * *